US007968106B2

(12) United States Patent
Francois et al.

(10) Patent No.: US 7,968,106 B2
(45) Date of Patent: Jun. 28, 2011

(54) **ABFB-1 GENE OF *PENICILLIUM FUNICULOSUM***

(75) Inventors: Jean Marie Francois, Castenet-Tolosan (FR); Jean-Luc G. Parrou, Toulouse (FR); Olivier Tourrasse, Toulouse (FR); Olivier Nore, Vernou sur Brenne (FR)

(73) Assignee: Adisseo France S.A.S., Anthony (FR)

( * ) Notice: Subject to any disclaimer, the term of this patent is extended or adjusted under 35 U.S.C. 154(b) by 651 days.

(21) Appl. No.: 11/918,525

(22) PCT Filed: May 3, 2006

(86) PCT No.: PCT/FR2006/000998
§ 371 (c)(1),
(2), (4) Date: Feb. 25, 2008

(87) PCT Pub. No.: WO2006/117482
PCT Pub. Date: Nov. 9, 2006

(65) Prior Publication Data
US 2009/0155418 A1 Jun. 18, 2009

(30) Foreign Application Priority Data

May 4, 2005 (FR) ..................................... 05 04562

(51) Int. Cl.
*A61K 39/00* (2006.01)
*A61K 38/43* (2006.01)
*A61K 38/00* (2006.01)
*A23K 1/17* (2006.01)
*C07K 1/00* (2006.01)
(52) U.S. Cl. .................. 424/274.1; 424/185.1; 424/442; 424/94.1; 530/350; 530/300; 530/823
(58) Field of Classification Search .................. None
See application file for complete search history.

(56) References Cited

U.S. PATENT DOCUMENTS
5,863,783 A * 1/1999 Van Heuvel et al. .......... 435/200

FOREIGN PATENT DOCUMENTS
WO    WO 99/57325 A2    11/1999
WO    WO 2004/018662 A2    3/2004

OTHER PUBLICATIONS

Carvallo et al., "Characterization of an α-L-arabinofuranosidase gene (abfl) from *Penicillium purpurogenum* and its expression", *Mycological Research*, vol. 107, No. 4 pp. 388-394, Apr. 2003.

De Ioannes et al., "An α-L-arabinofuranosidase from *Penicillium purpurogenum*: production, purification and properties", *Journal of Biotechnology*, vol. 76, No. 2-3, pp. 253-258, Jan. 21, 2000.
Park et al., "A new method for the preparation of crystalline L-arabinose from arabinoxylan by enzymatic hydrolysis and selective fermentation with yeast", *Biotechnology Letters*, vol. 23, No. 5 pp. 411-416, Mar. 2001.
Le Clinche et al., "α-L-Arabinofuranosidase from *Aspergillus terreus* with Potential Application in Enology: Induction, Purification, Characterization", *Journal of Agricultural and Food Chemistry*, vol. 45, No. 7, pp. 2379-2383, Jul. 1997.
Hashimoto et al., "α-L-Arabinofuranosidase of *Aspergillus oryzae* HL15", EMBL/GenBank/DDBJ databases, No. AB073860, Nov. 14, 2001.
Hashimoto et al., "α-L-Arabinofuranosidas B", EMBL/GenBank/ DDBJ databases, No. Q96VA1, Dec. 1, 2001.
Margolles-Clark et al., "Cloning of Genes Encoding α-L-Arabinofuranosidase and β-Xylosidase from *Trichoderma reesei* by Expression in *Saccharomyces cerevisiae*", *Applied and Environmental Microbiology*, vol. 62, No. 10, pp. 3840-3846, Oct. 1996.
Sakamoto et al., "Molecular characterization of a *Penicillium chrysogenum* exo-1,5-α-L-arabinanase that is structurally distinct from arabinan-degrading enzymes", *FEBS Letters*, vol. 560, pp. 199-204 (2004).
Koseki et al., "Role of Two α-L-Arabinofuranosidases in Arabinoxylan Degradation and Characteristics of the Encoding Genes from Shochu Koji Molds, *Aspergillus kawachii* and *Aspergillus awamori*", *Journal of Bioscience and Bioengineering*, vol. 96, No. 3, pp. 232-241 (2003).
Gielkens et al., "The abfB gene encoding the major α-L-arabinofuranosidase of *Aspergillus nidulans*: nucleotide sequence, regulation and construction of a disrupted strain", *Microbiology*, vol. 145, pp. 735-741 (1999).
Brice et al., "The degradation of isolated hemiculluloses and ligninhemicullulose complexes by cell-free, rumen hemicellulases", *Carbohydrate Research*, vol. 101, pp. 93-100 (1982).
Panagiotou et al., "Induction, purification, and characterization of two extracellular α-L-arabinofuranosidases from *Fusarium oxysporum*", *Canadian Journal of Microbiology*, vol. 49, pp. 639-644 (2003).

\* cited by examiner

*Primary Examiner* — S. Devi
(74) *Attorney, Agent, or Firm* — Oliff & Berridge, PLC

(57) ABSTRACT

The invention relates to the abfB-1 gene of *Penicillium funiculosum* that codes for a type B α-L-arabinofuranosidase. This enzyme α-L-arabinofuranosidase can be incorporated in nutritional additives or in foods for animals for which it improves the digestibility and thus the nutritional value.

10 Claims, 4 Drawing Sheets

ABFB-1 GENE OF *PENICILLIUM FUNICULOSUM*

The invention relates to the abfB-1 gene isolated from *Penicillium funiculosum* and the ABFB-1 polypeptide encoded by this gene having an α-L-arabinofuranosidase B activity.

*Penicillium funiculosum* is a Talaromyces belonging to the Aspergilleae family. The isolation of this microorganism from numerous organic substrates which are subject to aerial or aqueous contamination shows that this fungus possesses a range of hydrolytic enzymes of a surprising richness. The use of this enzymatic cocktail in animal feed contributes towards the depolymerization of the natural organic substances and makes it possible to improve their digestibility. WO 99/57325 thus describes a *Penicillium funiculosum* strain called IMI378536 which produces a mixture of enzymes which is particularly suitable as animal feed. However, the enzymatic cocktails produced by *Penicillium funiculosum* have not been biochemically characterized to any great extent. Indeed, only a limited number of enzymatic activities, such as xylanases and β-glucanases are generally measured on the fermentation broths obtained. These activities reflect only a fraction of the enzymatic population present in the cocktail.

Hemicellulolytic compounds derived from agriculture constitute the second polysaccharide reserve after cellulose in plant tissues. This group is characterized by a wide variety of heteropolysaccharides, of which the principle representatives are xylans, arabinans, galactans, glucans and mannans. Arabinose, in its furfural form, is widely represented among the heteropolysaccharides such as arabinans and arabinoxylans. Arabinan is a polymer with arabinofuranose residues linked by α-1-5 bonds and it may be substituted with 1 or 2 arabinose residues at the O-2 or O-3 position. As regards the arabinoxylans, the α-L-arabinofuranosyl residues are linked to the principle β-1-4-xylopyranosyl chain by α-1-3 and α-1-2 bonds. The presence of arabinose residues on these side chains can restrict the enzymatic hydrolysis of hemicellulolytic compounds in numerous industrial applications such as the enhancement of the digestibility of animal feed. The enzymes cleaving the α-L-arabinofuranoside bonds can act in synergy with xylanases to allow the hydrolysis of arabinoxylans and arabinans.

The arabinase activities (endo-, exo-arabinase and, predominantly, the α-L-arabinofuranosidase activities) can therefore actively and synergistically contribute, with the xylanases, to the depolymerization of the hemicellulolytic compounds. The hemicellulolytic and pectic compounds may represent up to 50% of the total carbohydrates present in plants and they constitute a major source of energy for animals. The enhancement of the digestibility of these compounds is correlated with the decrease in the degree of substitution of the arabinosyl residues within the hemicellulolytic compounds (Brice, R. E., Morrison, I. M. 1982, Carbohydr. Res. 101: 93-100).

The enzymes which hydrolyse the bonds between L-arabinose residues have been isolated from microorganisms such as bacteria or filamentous fungi. Arabinosidases consist mainly of α-L-arabinofuranosidases (EC 3.2.1.55) which are capable of hydrolysing the non-reducing α-L-arabinofuranosyl residues derived from L-arabinoxylan or compounds such as arabinans and arabinogalactans.

The α-L-arabinofuranosidases (EC 3.2.1.55) have been classified into two families of Glycoside Hydrolases (GH 51 and GH 54) according to their protein sequence similarities. These two families differ by virtue of their specificity for substrate contained in polysaccharides. The first group (GH 51) contains type A arabinofuranosidases which act only on small linear structures of α-1-5 linked arabinofuranosyl oligosaccharides. The second group consists of type B arabinofuranosidases (GH 54) which catalyse the hydrolysis of the α-1,5, α-1,3 and α-1,2 bonds of the side chains contained in the arabinofuranosyl-oligosaccharide compounds.

The B arabinofuranosidases (ABFB) have been isolated from numerous bacteria, but also from filamentous fungi. The genus *Aspergillus* is the most widely represented, but they have also been isolated from the genera *Trichoderma*, *Penicillium* and *Fusarium*.

WO 96/29416, WO 96/06935, Wo 2004/018662 and U.S. Pat. No. 5,989,887 describe *Aspergillus niger* arabino-furanosidase genes. The protein sequence alignment indicates that the *A. niger* abfB protein is 72.4% identical to the *P. funiculosum* ABFB-1 protein. None of the characteristics essential for the use of the polypeptide in animal nutrition is described in these applications.

Clinche et al. (J. Agric. Food Chem., 45, 2379-2383, 1997) have described three α-L-arabinofuranosidases derived from *Aspergillus terreus* having a potential application in oenology.

Gielkens et al. (Microbiology, 145, 735-741, 1999) have described the *Aspergillus nidulans* abfB gene.

The *Aspergillus kawachii* and *Aspergillus awamori* abfB genes have been described by Koseki et al. (J. of Bioscience and Bioengineering, Vol. 96, No. 3, 232-241, 2003). These enzymes have applications in the fermentation of the Japanese liquor shochu.

The abfB gene from the filamentous fungus *Trichoderma reesei* has been described by Margolles-Clark et al. (Applied and Environmental Microbiology, 3840-3846, 1996).

Panagiotou et al. have also described two extracellular alpha-L-arabinofuranosidases derived from *Fusarium oxysporum* (Can J. Microbiol. 2003: 49(10): 639-4).

Carvallo et al. (Mycol. Res., 107 (4), 388-394, 2003) have described the B α-L-arabinofuranosidase from *Penicillium purpurogenum*. The protein sequence alignment indicates that the *P. purpurogenum* abf-1 protein is 85.6% identical to the *P. funiculosum* ABFB-1 protein. None of the characteristics essential for the use of the polypeptide in animal nutrition is described in this article.

Sakamoto et al. (FEBS Letters 560, 199-204, 2004) have described the *Penicillium chrysogenum* abnx gene encoding nevertheless an arabinase activity distinct from the ABFB activity.

However, these ABFB enzymes do not have the optimum qualities required for application in animal feed. Indeed, to be utilizable in animal feed, the ABFBs must possess properties compatible with the treatments to which the feedingstuffs intended for this feed are subjected. In particular, the activity of the enzymes used must be stable under the process temperature and pH conditions, and, if possible, be optimum in the preparation of these feedingstuffs and under the conditions which exist in the digestive system of the animals ingesting these feedingstuffs.

Furthermore, these enzymes must have a broad spectrum of action (debranching) on the heteropolysaccharides (arabinans, arabinoxylans and arabinogalactans) to allow effective enhancement of the digestibility of the feedingstuffs by the animals. This enhancement of the digestibility of the feedingstuffs makes it possible to increase their nutritional value. Accordingly, the enzymes having enhanced specificity (stereospecificity, enantioselectivity), activity or affinity towards the natural substrates arabinoxylans and arabinans are of great interest as animal feed.

The present invention describes a *Penicillium funiculosum* L-arabinofuranosidase B (ABFB-1) suitable for application in animal nutrition and the gene encoding this enzyme. The invention also relates to the homologues, variants and fragments of ABFB-1 preserving the same catalytic properties.

Advantageously, the ABFB enzymes according to the invention have a high optimum temperature.

Another advantage of the present invention is that the expression of the *Penicillium funiculosum* ABFB-1 is naturally highly induced in this fungus under conditions for the induction of cellulolytic and hemicellulolytic enzymes (industrial-type culture medium for the production of cellulolytic and hemicellulolytic enzymes).

The enzymes according to the invention also have other industrial or agroindustrial applications. There may be mentioned in particular the treatment of fruit juices, the manufacture of paper, the conversion of hemicellulolytic biomass to fuel or chemical products, the preparation of alcoholic drinks by fermentation.

Description of the Sequences

SEQ ID No. 1: Genomic sequence of the *Penicillium funiculosum* abfB-1 gene.

SEQ ID No. 2: Sequence of the *Penicillium funiculosum* ABFB-1 polypeptide having type B α-L-arabinofuranosidase activity.

SEQ ID No. 3: XbaI-abfB primer.

SEQ ID No. 4: HindIII-abfB primer.

DESCRIPTION OF THE INVENTION

The present invention relates to a polypeptide suitable for use in animal nutrition comprising a polypeptide chosen from the following polypeptides:
 the polypeptide of SEQ ID No. 2,
 the polypeptide whose sequence is between position 28 and position 507 of SEQ ID No. 2,
 a fragment of the polypeptide of SEQ ID No. 2 having an α-L-arabinofuranosidase B activity,
 a polypeptide having an α-L-arabinofuranosidase B activity and exhibiting at least 90% identity with the polypeptide of SEQ ID No. 2.

The invention also relates to a polynucleotide, encoding an α-L-arabinofuranosidase B activity, chosen from the following polynucleotides:
 the polynucleotide whose sequence is between position 845 and position 2368 of SEQ ID No. 1,
 the polynucleotide whose sequence is between position 927 and position 2368 of SEQ ID No. 1,
 a polynucleotide encoding a polypeptide as defined above.

Another subject of the present invention is a polynucleotide having the sequence represented by SEQ ID No. 1 or the sequence complementary to SEQ ID No. 1.

The invention also relates to expression cassettes comprising, in the direction of transcription:
 a promoter that is functional in a host organism;
 a polynucleotide according to the invention; and
 a terminator sequence that is functional in the same host organism.

Another subject of the invention is a vector comprising a polynucleotide according to the invention and/or an expression cassette according to the invention.

The invention also relates to a host organism transformed with a polynucleotide according to the invention, an expression cassette according to the invention and/or a vector according to the invention.

In one embodiment of the invention, the host organism is chosen from yeasts and filamentous fungi.

Preferably, the host organism is a *Penicillium funiculosum* strain.

The invention also relates to a nutritional additive for animals, comprising a polypeptide according to the invention, a host organism according to the invention or a fermentation broth of a host organism according to the invention.

Preferably, this nutritional additive is in liquid form or in powdered form.

Another aspect of the invention is a feedingstuff comprising a nutritional base for animals and a nutritional additive for animals according to the invention.

The invention also relates to the use of an ABFB polypeptide according to the invention or a host organism according to the invention for the manufacture of a nutritional additive for animals or of a feedingstuff.

Another subject of the invention is the use of an ABFB polypeptide according to the invention or of a host organism according to the invention for hydrolysing the α-L-arabinofuranosyl bonds of arabinofuranosyl-oligosaccharide compounds.

Polypeptides

The present invention therefore relates to ABFB polypeptides having an α-L-arabinofuranosidase B activity. Preferably, these polypeptides are isolated from *Penicillium funiculosum*.

The expression "α-L-arabinofuranosidase B" is understood to mean α-L-arabinofuranosidases (EC 3.2.1.55) type B (GH 54) which catalyse the hydrolysis of α-1,5, α-1,3 and α-1,2 bonds of the side chains contained in arabinofuranosyl-oligosaccharide compounds.

The α-L-arabinofuranosidase B of the *Penicillium funiculosum* strain IMI378536 is represented in SEQ ID No. 2.

The expression "polypeptide suitable for use in animal nutrition" is understood to mean a polypeptide whose characteristics are such that it is suitable for animal nutrition. The characteristics essential for use in animal nutrition are in particular the pH and the temperature at which the enzyme is active. Indeed, the pH of the digestive system of the animals is acidic and it is therefore essential that the enzyme remains active at this pH, this being in order to preserve its activity in the hydrolysis of the L-arabinose residues. In addition, conditioning the enzyme in a nutritional additive or in the animal feed involves treatments and a temperature greater than room temperature. The activity of the enzymes used must therefore be stable under the process conditions, and in particular the temperature conditions.

According to one embodiment of the present invention, the polypeptide exhibits an α-L-arabinofuranosidase B activity at an acidic pH, for example less than 5, preferably less than 4. Also, according to one embodiment of the present invention, the polypeptide exhibits an optimum α-L-arabinofuranosidase B activity between pH 2 and pH 3.5.

According to a preferred embodiment of the present invention, the polypeptide exhibits an α-L-arabino-furanosidase B activity at temperatures greater than room temperature. Preferably, the polypeptide of the present invention has an optimum α-L-arabino-furanosidase B activity at a temperature of between 40° C. and 70° C., more preferably between 50° C. and 65° C.

In a preferred embodiment, the polypeptides according to the invention are glycosylated. The polypeptide of SEQ ID No. 2 possesses in particular N-glycosylation sites at amino acid 92 and at amino acid 376. In a preferred embodiment, the asparagin residues at position 92 and 376 of the polypeptide of SEQ ID No. 2 are glycosylated.

The α-L-arabinofuranosidase B of *Penicillium funiculosum* is an enzyme secreted by the fungus into its extracellular environment. The polypeptide of SEQ ID No. 2 thus comprises a signal peptide of 27 amino acids. The subject of the invention is also the mature polypeptide obtained after cleaving the signal peptide.

In particular, the invention relates to the polypeptide whose sequence is between position 28 and position 507 of SEQ ID No. 2. In another embodiment, the signal peptide of the polypeptide of SEQ ID No. 2 may be replaced by a heterologous signal peptide for the expression and the secretion of the polypeptide of SEQ ID No. 2 by a heterologous host organism.

The invention also relates to fragments of the polypeptide of SEQ ID No. 2 having an α-L-arabinofuranosidase B activity.

The term "fragment" of a polypeptide denotes a polypeptide comprising a portion but not the entire polypeptide from which it is derived. The invention thus relates to a polypeptide comprising a fragment of at least 100, 200, 300, 400 or 500 amino acids of the polypeptide of SEQ ID No. 2.

This fragment of the polypeptide of SEQ ID No. 2 preserves its α-L-arabinofuranosidase B activity. The invention therefore relates to the biologically active fragments of the polypeptide of SEQ ID No. 2. The term "biologically active fragment" denotes a fragment of a polypeptide preserving the function of the polypeptide from which it is derived. The biologically active fragments of the polypeptide of SEQ ID No. 2 thus preserve the function of the *Penicillium funiculosum* ABFB-1 polypeptide. These biologically active fragments have an α-L-arabinofuranosidase B activity.

The methods for preparing fragments of a polypeptide and the techniques for measuring the α-L-arabinofuranosidase B activity are well known to a person skilled in the art.

The subject of the invention is also polypeptides having an L-arabinofuranosidase B activity and exhibiting at least 90% identity with the polypeptide of SEQ ID No. 2. Preferably, these polypeptides have the same properties and in particular the same catalytic properties as the polypeptides of SEQ ID No. 2. Preferably, these polypeptides are isolated from other strains of *Penicillium funiculosum* or from other filamentous fungi. Alternatively, these polypeptides may be obtained by site-directed mutagenesis techniques for example.

The subject of the invention is polypeptides having at least 90%, 95%, 98% and preferably at least 99% of amino acids that are identical with the polypeptide of SEQ ID No. 2.

The expression identical amino acids is understood to mean amino acids that are invariant or unchanged between two sequences. These polypeptides may exhibit a deletion, an addition or a substitution of at least one amino acid compared with the polypeptide of SEQ ID No. 2.

The subject of the invention is also polypeptides exhibiting at least 90%, 95%, 98% and preferably at least 99% similarity with the polypeptide of SEQ ID No. 2.

The expression similarity is understood to mean the measurement of the resemblance between proteic or nucleic sequences. These polypeptides may exhibit a deletion, an addition or a substitution of at least one amino acid compared with the polypeptide of SEQ ID No. 2. The degree of similarity between two sequences, quantified by a score, is based on the percentage sequence identity and/or sequence-preserving substitutions.

Methods for measuring and identifying the degree of identity and the degree of similarity between polypeptides are known to persons skilled in the art. It is possible to use for example Vector NTi 9.1.0, the alignment programme AlignX (Clustal W algorithm) (Invitrogen INFORMAX). Preferably, the default parameters are used.

The polypeptides according to the invention are isolated or purified from their natural environment. The polypeptides may be prepared by means of various methods. These methods are in particular purification from natural sources such as cells naturally expressing these polypeptides, the production of recombinant polypeptides by appropriate host cells and their subsequent purification, production by chemical synthesis or, finally, a combination of these various approaches. These various methods of production are well known to persons skilled in the art. Thus, the ABFB polypeptides of the present invention may be isolated from *Penicillium funiculosum*. In another embodiment, the ABFB polypeptides of the present invention are isolated from recombinant host organisms expressing an ABFB polypeptide according to the invention.

The subject of the invention is also fusion proteins, recombinant proteins or chimeric proteins comprising the polypeptides according to the invention. The term "polypeptide" also denotes modified proteins and polypeptides.

The polypeptides according to the invention have an ABFB activity and preferably preserve the catalytic properties of the *Penicillium funiculosum* ABFB-1 enzyme. In particular, these polypeptides have an optimum activity at 60° C. and at pH 3.4.

Polynucleotides

The invention also relates to polynucleotides encoding an α-L-arabinofuranosidase B activity. Preferably, these polynucleotides encode a *Penicillium funiculosum* α-L-arabinofuranosidase B.

According to the present invention, the expression "polynucleotide" is understood to mean a single-stranded nucleotide chain or its complementary strand which may be of the DNA or RNA type, or a double-stranded nucleotide chain which may be of the complementary or genomic DNA type. Preferably, the polynucleotides of the invention are of the DNA type, in particular double-stranded DNA. The term "polynucleotide" also denotes the modified polynucleotides.

The polynucleotides of the present invention are isolated or purified from their natural environment. Preferably, the polynucleotides of the present invention may be prepared by conventional molecular biology techniques as described by Sambrook et al. (Molecular Cloning: A Laboratory Manual, 1989) or by chemical synthesis.

In a first embodiment, the invention relates to the polynucleotide whose sequence is between position 845 and position 2368 of SEQ ID No. 1. This polynucleotide encodes the *Penicillium funiculosum* ABFB-1 enzyme of SEQ ID No. 2.

In a second embodiment, the invention relates to the polynucleotide whose sequence is between position 927 and position 2368 of SEQ ID No. 1. This polynucleotide encodes the *Penicillium funiculosum* mature ABFB polypeptide after cleavage of the signal peptide.

The invention also relates to polynucleotides having at least 70%, 75%, 80%, 85%, 90%, 95%, 98% and preferably at least 99% identity with the polynucleotide whose sequence is between position 845 and position 2368 of SEQ ID No. 1 and/or with the polynucleotide whose sequence is between position 927 and position 2368 of SEQ ID No. 1. These polynucleotides encode an α-L-arabinofuranosidase B activity. Preferably, these polynucleotides encode a *Penicillium funiculosum* α-L-arabinofuranosidase B.

The expression identical nucleotides is understood to mean nucleotides that are invariant or unchanged between two sequences. These polynucleotides may exhibit a deletion, an addition or a substitution of at least one nucleotide compared with the reference polynucleotide.

The invention also relates to polynucleotides exhibiting at least 70%, 75%, 80%, 85%, 90%, 95%, 98% and preferably at least 99% similarity with the polynucleotide whose sequence is between position 845 and position 2368 of SEQ ID No. 1 and/or with the polynucleotide whose sequence is between position 927 and position 2368 of SEQ ID No. 1. These polynucleotides encode an α-L-arabinofuranosidase B activity. Preferably, these polynucleotides encode a *Penicillium funiculosum* α-L-arabinofuranosidase B.

The expression similarity is understood to mean the measurement of the resemblance between protein or nucleic sequences. These polynucleotides may exhibit a deletion, an addition or a substitution of at least one nucleotide compared with the reference polynucleotide. The degree of similarity between two sequences, quantified by a score, is based on the percentage sequence identity and/or sequence-preserving substitution.

The methods for measuring and identifying the degree of identity and the degree of similarity between nucleic acid sequences are well known to persons skilled in the art. It is possible to use for example Vector NTi Vector NTi 9.1.0, an alignment programme AlignX (Clustal W algorithm) (Invitrogen INFORMAX). Preferably, the default parameters are used.

Preferably, the polynucleotides exhibiting a degree of similarity with a reference polynucleotide preserve the function of the reference sequence. In the present case, the polynucleotides encode an α-L-arabinofuranosidase B activity.

The invention also relates to polynucleotides capable of selectively hybridizing with the polynucleotide whose sequence is between position 845 and position 2368 of SEQ ID No. 1 and/or with the polynucleotide whose sequence is between position 927 and position 2368 of SEQ ID No. 1. Preferably, the selective hybridization is carried out under conditions of average stringency and preferably under conditions of high stringency. These polynucleotides encode an α-L-arabinofuranosidase B activity. Preferably, these polynucleotides encode a *Penicillium funiculosum* α-L-arabinofuranosidase B.

The expression "sequence capable of selectively hybridizing" is understood to mean, according to the invention, the sequences which hybridize with the reference sequence at a level significantly above the background noise. The level of the signal generated by the interaction between the sequence capable of selectively hybridizing and the reference sequences is generally 10 times, preferably 100 times more intense than that of the interaction of the other DNA sequences generating the background noise. Stringent hybridization conditions allowing selective hybridization are well known to persons skilled in the art. In general, the hybridization and washing temperature is at least 5° C. less than the Tm of the reference sequence at a given pH and for a given ionic strength. Typically, the hybridization temperature is at least 30° C. for a polynucleotide of 15 to 50 nucleotides and at least 60° C. for a polynucleotide of more than 50 nucleotides. By way of example, the hybridization is carried out in the following buffer: 6×SSC, 50 mM Tris-HCl (pH 7.5), 1 mM EDTA, 0.02% PVP, 0.02%FICOLL, 0.02% BSA, 500 µg/ml denatured salmon sperm DNA. The washings are for example carried out successively at low stringency in a 2×SSC, 0.1% SDS buffer, at average stringency in a 0.5×SSC, 0.1% SDS buffer and at high stringency in a 0.1×SSC, 0.1% SDS buffer. The hybridization may of course be carried out according to other customary methods well known to persons skilled in the art (see in particular Sambrook et al., Molecular Cloning: A Laboratory Manual, 1989). Preferably, the polynucleotides selectively hybridizing with a reference polynucleotide preserving the function of the reference sequence. In the present case, the polynucleotides, which selectively hybridize with the polynucleotide whose sequence is between position 845 and position 2368 of SEQ ID No. 1 and/or with the polynucleotide whose sequence is between position 927 and position 2368 of SEQ ID No. 1, encode an α-L-arabinofuranosidase B activity.

The invention generally relates to the polynucleotides encoding the polypeptides according to the invention. Because of the degeneracy of the genetic code, various polynucleotides can encode the same polypeptide.

Another subject of the present invention is a polynucleotide whose sequence is represented in SEQ ID No. 1. The polynucleotide of SEQ ID No. 1 comprises sequences flanking the open reading frame (ORF) of the *Penicillium funiculosum* abfB-1 gene. They are in particular promoter and terminator sequences of the abfB-1 gene. The abfB gene may be expressed from its homologous regulatory sequences, in particular for overexpression in *Penicillium funiculosum* or in other filamentous fungi.

In another embodiment, the abfB gene may be expressed in various host organisms such as bacteria, yeasts and fungi for example. The abfB gene may be expressed in a host organism under the control of the promoter of SEQ ID No. 1 of the present invention or under the control of a heterologous promoter.

Expression Cassettes

According to one embodiment of the invention, a polynucleotide encoding a polypeptide according to the invention is inserted into an expression cassette using cloning techniques well known to persons skilled in the art. This expression cassette comprises the elements necessary for the transcription and the translation of the sequences encoding the polypeptides according to the invention.

Advantageously, this expression cassette comprises both elements which make it possible to cause a host cell to produce a polypeptide and elements necessary for the regulation of this expression.

These expression cassettes comprise, in the direction of transcription:
 a promoter that is functional in a host organism;
 a polynucleotide according to the invention;
 a terminator sequence that is functional in the same host organism.

Any type of promoter sequence may be used in the expression cassettes according to the invention. The choice of the promoter will depend in particular on the host organism chosen for the expression of the gene of interest. Some promoters allow a constitutive expression whereas other promoters are on the contrary inducible. Among the promoters that are functional in fungi, there may be mentioned in particular that for *Aspergillus nidulans* glyceraldehyde-3-phosphate dehydrogenase (Roberts et al., Current Genet. 15: 177-180, 1989). Among the promoters that are functional in bacteria, there may be mentioned in particular that for the T7 bacteriophage RNA polymerase (Studier et al., Methods in enzymology 185: 60-89, 1990). Among the promoters that are functional in yeasts, there may be mentioned the promoter for the GALL gene (Elledge et al., Proc Natl Acad Sciences, USA. 88: 1731-1735, 1991) or the *S. cerevisiae* GAL4 and ADH promoters. All these promoters are described in the literature and are well known to persons skilled in the art.

For expression in *Penicillium funiculosum*, expression cassettes will be chosen for example that comprise a histone H4.B promoter, an aspartyl acid protease promoter or a csl13 promoter (WO 00/68401).

The expression cassettes according to the present invention may additionally include any other sequence necessary for the expression of the polypeptides or polynucleotides, such as for example regulatory elements or signal sequences allowing the secretion of the polypeptides produced by the host organism. It is possible to use in particular any regulatory sequence that makes it possible to increase the level of expression of the coding sequence inserted into the expression cassette. According to the invention, it is possible to use in particular, in combination with the regulatory promoter sequence, other regulatory sequences, which are located between the promoter and the coding sequence, such as transcription activators ("enhancer").

A wide variety of terminator sequences can be used in the expression cassettes according to the invention, these sequences allow the termination of transcription and the polyadenylation of the mRNA. Any terminator sequence that is functional in the selected host organism may be used.

For expression in *Penicillium funiculosum*, expression cassettes will be chosen for example that comprise a histone H4.B terminator, an aspartyl acid protease terminator or a csl13 terminator (WO 00/68401).

The subject of the present invention is also a polynucleotide comprising an expression cassette according to the invention, advantageously the expression cassettes according to the present invention are inserted into a vector.

Vectors

The present invention therefore also relates to replicating or expression vectors for transforming a host organism comprising at least one polynucleotide or one expression cassette according to the present invention. This vector may correspond in particular to a plasmid, a cosmid, a bacteriophage or a virus into which a polynucleotide or an expression cassette according to the invention has been inserted. The techniques for constructing these vectors and for inserting a polynucleotide of the invention into these vectors are well known to persons skilled in the art. In general, it is possible to use any vector capable of maintaining itself, self-replicating or propagating in a host cell in order to induce in particular the expression of a polynucleotide or of a polypeptide. Persons skilled in the art will choose the appropriate vectors according to the host organism to be transformed, and according to the transformation technique used.

The vectors of the present invention are used in particular to transform a host organism for replication of the vector and/or the expression of a polypeptide according to the invention in the host organism.

The invention also relates to a method for preparing a polypeptide according to the invention comprising the following steps:
  a host organism is transformed with an expression vector comprising an expression cassette according to the invention and/or with a polynucleotide according to the invention,
  the polypeptides produced by the host organism are isolated.

Host Organisms

The subject of the present invention is also a method for transforming a host organism by integrating into the said host organism at least one polynucleotide or an expression cassette or a vector according to the invention. The polynucleotide may be integrated into the genome of the host organism or can stably replicate in the host organism. Methods for transforming the host organisms are well known to persons skilled in the art and are well described in the literature.

The present invention also relates to a host organism transformed with a polynucleotide, an expression cassette or a vector according to the invention. The expression host organism is understood to mean in particular according to the invention any mono- or pluricellular, lower or higher, organism, chosen from bacteria, yeasts and fungi. The expression host organism is understood to mean a non-human organism. Advantageously, the yeasts are chosen from *Pichia pastoris, Saccharomyces cerevisae, Yarrowia lipolytica* and *Schwanniomyces occidentalis*. The fungi are chosen from *Aspergillus* and *Penicillium*, preferably from *Penicillium funiculosum, Trichoderma reesei, Aspergillus niger, Aspergillus awamori, Aspergillus kawachii* and *Trichoderma koningii*. In a preferred embodiment, the host organism is a *Penicillium funiculosum* strain in which an ABFB polypeptide according to the invention is expressed or overexpressed.

The techniques for constructing vectors, transforming host organisms and expressing heterologous proteins in these organisms are widely described in the literature (Ausubel F. M. et al., "Current Protocols in Molecular Biology" Volumes 1 and 2, Greene Publishing Associates and Wiley Interscience, 1989; T. Maniatis, E. F. Fritsch, J. Sambrook, Molecular Cloning A laboratory Handbook, 1982).

Food Additives and Feedingstuffs

The present invention therefore relates to food additives providing an α-L-arabinofuranosidase B activity. The intake of this type of enzymatic activity makes it possible to enhance the digestibility of the food and to increase its nutritional value.

The expression nutritional additive is understood to mean a substance that is intentionally added to a food, generally in small quantities, in order to improve its nutritional characteristics or its digestibility. The nutritional additives for animals may contain for example vitamins, mineral salts, amino acids and enzymes.

Typically, the nutritional additives for animals comprise a polypeptide according to the invention, a host organism according to the invention or a fermentation broth of a host organism according to the invention. Thus, the polypeptides having an α-L-arabinofuranosidase B activity according to the invention can be purified or isolated from a *Penicillium funiculosum* strain or from a recombinant host organism for the manufacture of a nutritional additive for animals. Alternatively, a *Penicillium funiculosum* strain or a host organism producing AbfB polypeptides may be used directly for the manufacture of a nutritional additive for animals. In a preferred embodiment of the invention, the culture supernatant or fermentation broth of a *Penicillium funiculosum* strain or of a host organism according to the invention is used for the manufacture of nutritional additives for animals. This embodiment is particularly advantageous when the ABFB polypeptides are secreted by the *Penicillium funiculosum* strain or the host organism. Usually, this culture supernatant is concentrated or freeze-dried for the manufacture of the nutritional additive.

Accordingly, the invention also relates to a method for preparing an ABFB enzyme comprising the following steps:
  a) culturing a *Penicillium funiculosum* strain or a transformed host organism according to the invention under conditions for inducing the expression of ABFBs,
  b) separating the culture supernatant comprising the ABFB enzyme.

This culture supernatant or fermentation broth may then be concentrated or freeze-dried for the formulation of a food additive or of a feedingstuff.

If the host organism does not secrete the ABFB enzyme in the culture medium, an additional step of opening the cells and purifying the cellular extract may be necessary.

The nutritional additives of the present invention comprise an α-L-arabinofuranosidase B activity but may also comprise other nutritional substances such as vitamins, amino acids or mineral salts.

The additives according to the invention increase the digestibility of the feedingstuffs, thus contributing to a better enhancement of the nutritional value of diets based on cereals (wheat, barley, maize, oat, rye and the like) and on oilcakes (soybean, sunflower, rapeseed and the like) in particular.

The present invention also relates to the feedingstuffs comprising a nutritional base and a nutritional additive according to the invention. These feedingstuffs are usually provided in the form of meals or granules into which the additives according to the invention are incorporated.

The expression feedingstuff is understood to mean anything that can serve as food for animals.

The feedingstuffs comprise a polypeptide according to the invention, a host organism according to the invention or a fermentation broth of a host organism according to the invention.

For intensive animal breeding, these feedingstuffs usually comprise a nutritional base and nutritional additives.

The expression nutritional base is understood to mean what constitutes the main part of the animal feed ration, consisting by way of example of a mixture of cereals, proteins and fat of animal and/or plant origin.

The nutritional bases for animals are suitable as feed for these animals and are well known to persons skilled in the art. Usually, these nutritional bases comprise, for example, maize, wheat, pea and soybean. These nutritional bases are suitable for the needs of the various animal species for which they are intended. These nutritional bases may already contain nutritional additives such as vitamins, mineral salts and amino acids.

In a preferred embodiment, the invention relates to feedingstuffs for monogastric animals and in particular for poultry and pigs. Poultry comprises in particular laying hens, broilers, turkeys and ducks. Pigs comprise in particular growing-finishing pigs and piglets.

EXAMPLES

Figure 1:
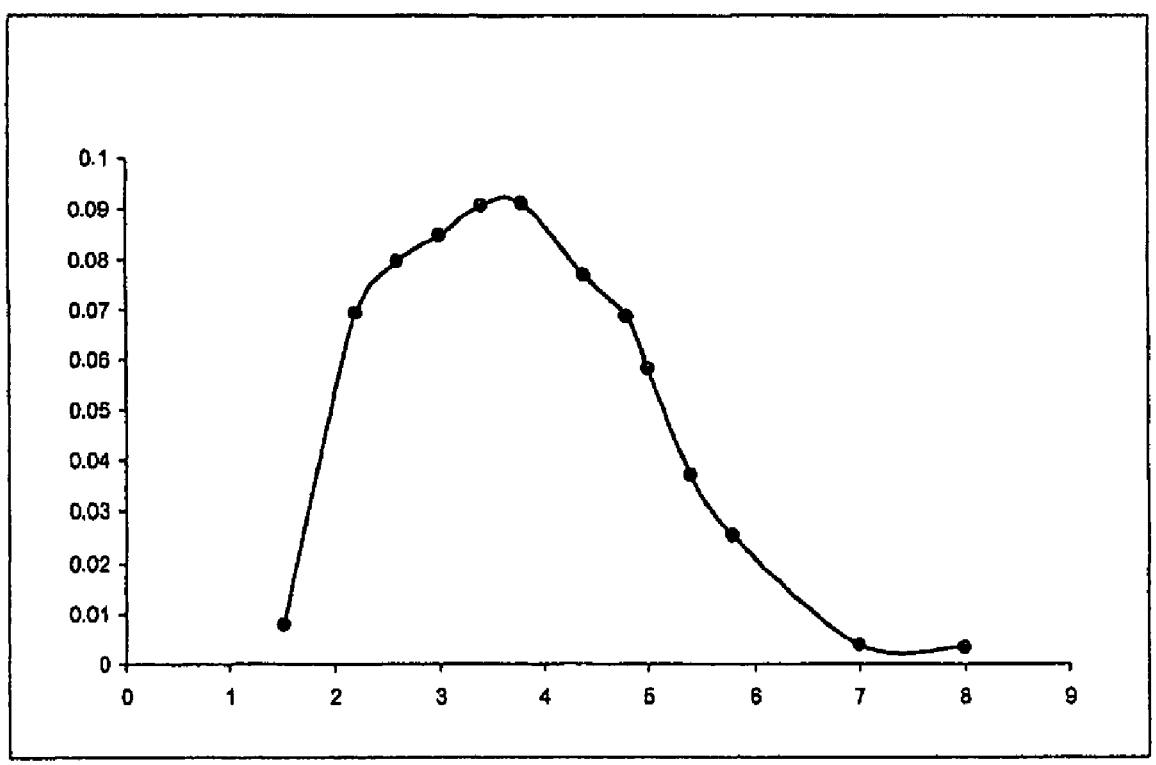
FIG. 1: Determination of the optimum pH of the ABFB-1 enzyme in a MCILVAINE buffer series (pH 2.2 to 8) at 40° C. in the presence of 5 mM PNPAF.

Development of the Assay of the L-arabinofuranosidase B Activity

The L-arabinofuranosidase activity was measured from a *P. funiculosum* culture on M2 medium with a mixed addition composed of 0.15% provasoy and 0.3% cellulose after 40 h. Samples were collected at 48 h and 72 h of culture. The culture was performed in a 200 ml Erlenmeyer flask with a useful volume of 50 ml. The activity was determined by hydrolysing 5 mM para-nitrophenyl-(L-arabinofuranoside (PNPAF) in a 50 mM sodium acetate buffer, pH 5. 50 µl of culture supernatant were incubated with 250 µl of substrate preheated at 50° C. for 15 min. The reaction was stopped by adding 500 µl of 0.5 M NaOH. The release of p-nitrophenyl (PNP) is measured at 405 nm with a molar extinction coefficient of 17 000 M-1. cm-1. An enzyme unit is defined as the quantity of enzyme which hydrolyses 1 µmol of PNPAF per minute under the conditions described above. For the culture of *P. funiculosum*, we obtained 20 mU . ml-1 after 48 h and 112 mU . ml-1 after 72 h of culture. These results are in agreement with the literature, indeed for *Aspergillus niger*, activities of the order of 100 to 600 mU . ml-1 were observed according to the inducer used in the culture.

Cloning of *P. funiculosum* abfB ORF into *Saccharomyces cerevisiae*

Starting with genomic DNA from *P. funiculosum*, the abfB gene was amplified by PCR with the aid of the pair of primers (HindIII-abfB/XbaI-abfB) under the following conditions (94° C. 30 sec; 62° C. 30 sec; 1 min 30 sec at 72° C.) for 30 cycles. The PCR product was cloned into a commercial vector pGEM-T™ easy.

Sequence of the PCR primer pair

```
XbaI-abfB-1:                          (SEQ ID NO: 3)
>5'-TCTAGAATGTTTCCAAGAATAAAACCAG-3'<

HindIII-abfB-1:                       (SEQ ID NO: 4)
>5'-AAGCTTTCATGCAAAGGCAGTCT-3'<
```

The HindIII/XbaI fragment of 1534 bp was excised from the vector pGEM-T and subcloned at the HindIII/XbaI sites into a shuttle vector pJL 52 (plac195-PGK/CYC1). For heterologous expression, the abfB gene is therefore under the control of the constitutive PGK promoter of the gene encoding phosphoglycerate kinase (*S. cerevisiae*) and the CYC1 terminator (*S. cerevisiae*) of the gene encoding a cytochrome C oxidase activity. The new expression cassette is called pOT-01.

The *S. cerevisiae* strain JF #1194 (CEN.PK113-5D), a clone derived from the strain CEN.PK 122 carrying the ura 3-52 auxotrophy, was transformed (lithium acetate/heat shock method) with the expression vector pOT-01. The transformant strains were selected by phenotype complementation on uracil-free selective plates (URA3 marker).

Six transformants were selected in order to test for the presence of an arabinofuranosidase B activity in the culture supernatant. The transformants were cultured in 50 ml of uracil-free YNB medium (except the wild-type control strain) for 24 hours. The arabinofuranosidase activity was assayed on the culture supernatants with the aid of the method described in the preceding paragraph.

Determination of the Optimum pH

The abfB-1 gene encoding an arabinofuranosidase B activity derived from *P. funiculosum* was cloned into *S. cerevisiae*. After checking for the presence of an arabinofuranosidase B activity in several transformants, a transformant was chosen and the ABFB activity was assayed on the culture supernatant after 24 h of growth. The cultures were carried out in a 200 ml Erlenmeyer flask (working volume 50 ml). The activity was determined in the presence of 5 mM p-nitrophenyl-α-L-arabinofuranoside (PNPAF) in a MCILVAINE buffer series (pH 2.2 to 8.0). 80 µl of culture supernatant were incubated with 320 µl of substrate preheated at 40° C. for 10 min. The reaction was stopped by adding 1 ml of 1M $Na_2CO_3$. The release of p-nitrophenyl is measured at 405 $nm^{-1}$. One enzyme unit is defined as the quantity of enzyme which hydrolyses 1 µmol of PNPAF per minute under the conditions defined above. The activity curve is represented in FIG. 1. For ABFB-1, the activity optimum is at pH 3.4 and the enzyme preserves 65% activity at pH 5.

Determination of the Optimum Temperature

Figure 2:
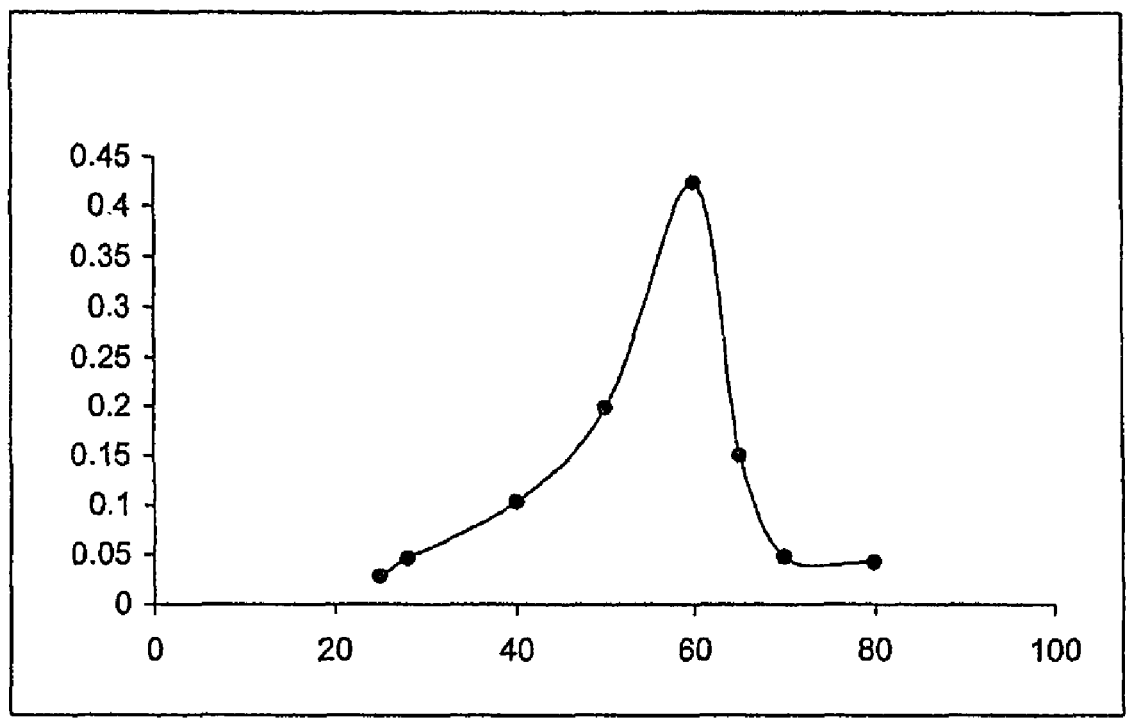
FIG. 2: Determination of the optimum temperature for the ABFB-1 enzyme at its optimum pH in the presence of 5 mM PNPAF.

Using the same protocol, we determined the optimum temperature for the activity of ABFB-1. The enzyme was incubated for 10 min at each of the temperatures in a McIlvaine buffer at pH 3.4. The activity curve is presented in FIG. 2. The *P. funiculosum* ABFB-1 has an activity optimum at 60° C. ABFB-1 therefore has a temperature optimum higher than the ABFBs described. If the optimum pH and temperature of the ABFB-1 enzyme are selected (pH 3.4 and 60° C.), it is observed that the activity for ABFB-1 is 4 times as high as the activity determined in an acetate buffer pH 5 and 40° C. (424 mU vs 102 mU).

Determination of $K_m$ and $V_m$

The kinetic constants ($K_m$ and $V_m$) for ABFB-1 were determined by measuring the hydrolysis of PNPAF over time, under the optimum conditions determined above.

Figure 3:
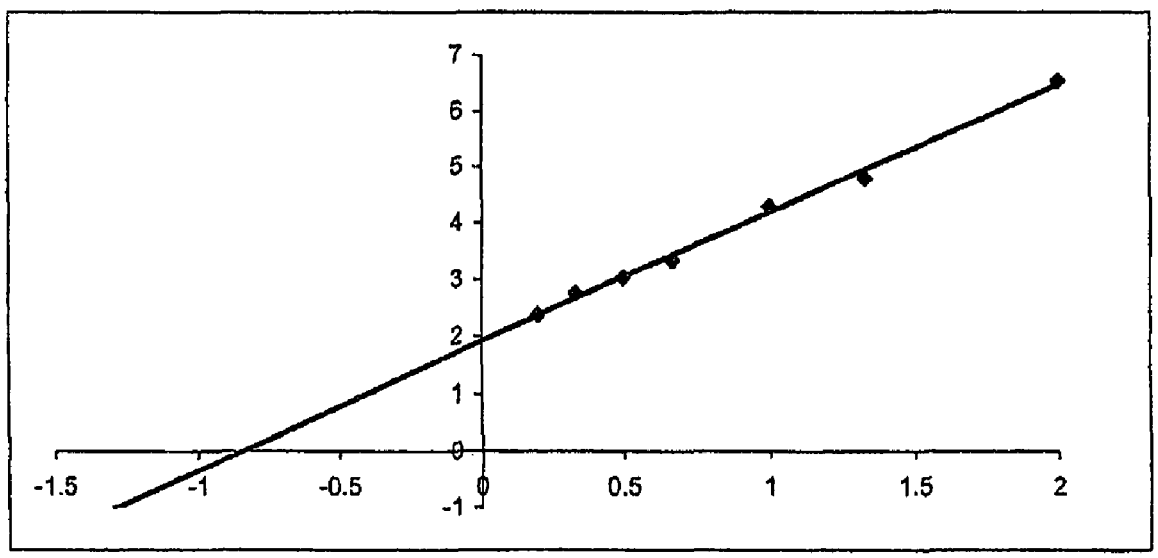
FIG. 3: Determination of the kinetic constants $K_m$ and $V_m$ (1/Vi=f(1/S)) for ABFB-1 for a PNPAF range from 0.5 mM to 5 mM at pH 3.4 and 60° C.

The substrate (PNPAF) concentration ranges were established between 0.5 and 5 mM in a pH 3.4 buffer. The kinetics of hydrolysis was monitored for 10 minutes at 60° C. The results were treated according to the double inverse method (Lineweark and Burk) and presented in FIG. 3.

The Km value is 1 mM for ABFB-1. By comparison, in the literature, the Km values for this type of enzyme varies from 0.05 to 1.2 mM according to the genus and the fungal species studied. ABFB-1 has a maximum speed of hydrolysis ($V_m$) of 521 mol PNPAF/mol of enzyme/min under the conditions described above.

Determination of the Molecular Weight of the ABFB-1 Enzyme

In order to determine the molecular weight of the ABFB-1 enzyme, the culture supernatant, derived from the growth of a mutant (*S. cerevisiae*) in a minimum medium, was concentrated 200-fold, denatured by boiling at 100° C. for 5 min, and then deposited in an SDS-polyacrylamide gel.

It is observed that the quantity of extracellular proteins is extremely low in the wild-type strain. For the mutants, the ABFB-1 enzyme is secreted into the culture supernatant. It is predominant in relation to the basal level of the *S. cerevisiae* extracellular proteins.

The determination of the molecular weight was carried out with the aid of the size marker SEEBLUE (Invitrogen). The results are presented in Table 1.

TABLE 1

ABFB-1 molecular weight in KDa

|  | Predicted MW | MW estimated on gel |
|---|---|---|
| ABFB-1 | 53 | 65 |

We compared the molecular weight predicted by the algorithm Vector NTi and the weight obtained by electrophoretic migration in a denaturing SDS-PAGE gel. We observed an overestimation of the molecular weight of the enzyme in the SDS-PAGE gel. A high glycosylation of the enzyme is indeed suggested by the visualization on gel of a diffuse electrophoretic band (O and N glycosylations). The glycosylations occur during the processing of the proteins in the expressing organism.

Analysis of the Profile of Expression of the abfB-1 Gene in *Penicillium funiculosum*

*Penicillium funiculosum* possesses two genes encoding B α-L-arabinofuranosidases: the abfB-1 and abfB-2 genes. The profiles of expression of these genes under various *P. funiculosum* culture conditions were compared.

*P. funiculosum* was cultured under conditions for inducing cellulolytic and hemicellulolytic enzymes (type M2 industrial growth medium) and under non-producing conditions (minimum glucose medium M0). After 40 h of growth, the cultures were stopped, the mycelium was recovered, and the total RNAs were extracted. The quantity and the quality of the RNAs were assessed by measuring the absorbance at 260 nm and at 280 nm (260/280 ratio>1.8). The level of transcripts encoding the B-type arabinofuranosidase (ABFB-1 and ABFB-2) activities were quantified under each of the two conditions (M0 and M2) by real-time quantitative PCR.

The gene encoding *P. funiculosum* tubulin (tub-1) was used as a control under the two conditions. This gene encodes a structural protein that is essential for the integrity of the cell. This gene is commonly used as the reference gene because it exhibits a constant level of expression regardless of the culture condition used (ubiquitous).

Specific primers for quantitative PCR were designed for each of the genes (abfB-1, abfB-2 and tub-1). For both growth conditions (M0 and M2), 2 µg of total RNA were retrotranscribed. A series of dilutions of the complementary DNAs derived from the retrotranscription were carried out in order to determine the optimum conditions for amplification of the target genes (constraints of the quantitative PCR method and for the efficiency of these pairs of primers).

Figure 4:
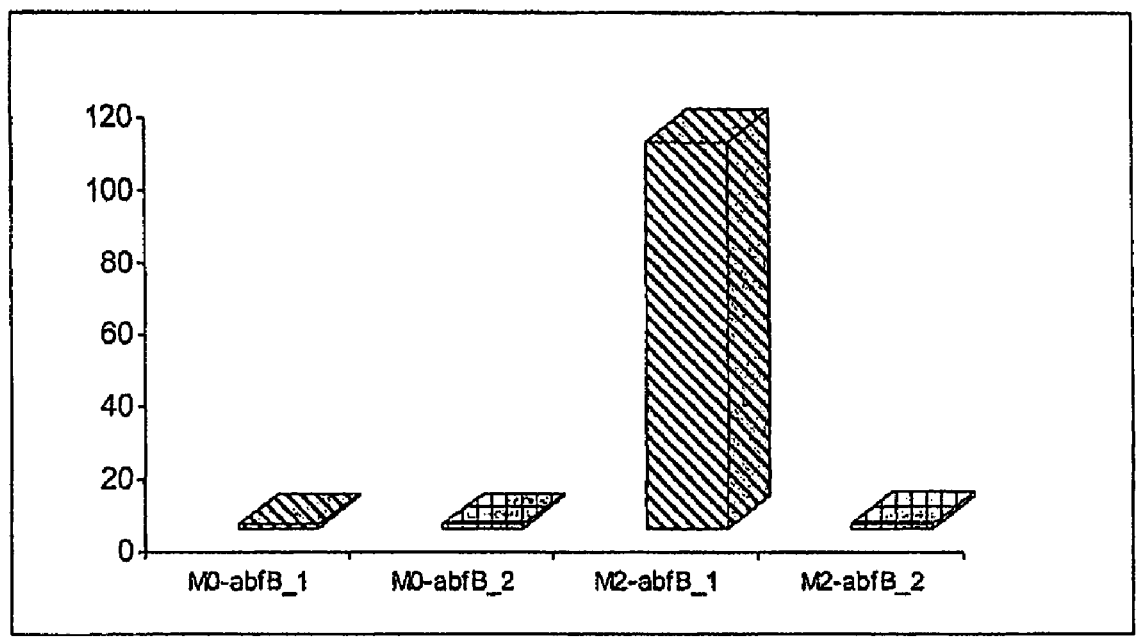
FIG. 4: Values of relative quantitative differential expression of the abfB-1 and abfB-2 genes according to the *P. funiculosum* growth conditions.

The normalized results are presented in Table 2 and FIG. 4.

TABLE 2

Values for differential expression of the abfB-1 and abfB-2 genes as a function of the *P. funiculosum* growth conditions

|  | M0 | M2 |
|---|---|---|
| abfb_1 | 1 | 107 |
| abfb_2 | 1 | 1.27 |

The transcriptional regulations of the genes encoding cellulolytic and hemicellulolytic activities have been described. The expression of these genes is highly subject to the nature and/or to the complexity of the carbon and nitrogen source on which the microorganism is cultured. A high transcriptional repression of these genes has been reported in the presence of glucose. This regulation is performed via a catabolic repression protein CreA which specifically binds to the promoter of these genes and blocks their transcription. In our experiment for quantifying, by PCR, the abfB-1 and abfB-2 messengers, that the level of expression of these two genes under the glucose (M0) condition is very low. This is in agreement with the literature since it has been shown that these genes have a basal level of expression even under unfavourable conditions (absence of cellulolytic and/or hemicellulolytic substrates). The results obtained for the M0 condition are in agreement with the literature. As regards the expression of the abfB-1 gene, an induction factor is observed that is 107 times as high as the basal level obtained under the M0 condition, whereas the abfB-2 gene is not overexpressed.

The invention claimed is:

1. An isolated polypeptide suitable for use in animal nutrition wherein the polypeptide is selected from the group consisting of:
   the polypeptide set forth in SEQ ID NO: 2, and
   the polypeptide the sequence of which is comprised between position 28 and position 507 of SEQ ID NO: 2.

2. Nutritional additive for animals, comprising the polypeptide according to claim 1.

3. The nutritional additive for animals according to claim 2, wherein the nutritional additive is in liquid form or in powdered form.

4. Feedingstuff, comprising a nutritional base for animals and the nutritional additive for animals according to claim 2.

5. A method of manufacturing a nutritional additive for animals, or a method of manufacturing a feedingstuff comprising incorporating the polypeptide of claim 1 into the additive or the feedingstuff.

6. A method of hydrolysing the α-L-arabinofuranosyl bonds of arabinofuranosyl-oligosaccharide compounds comprising contacting the compounds with the polypeptide of claim 1.

7. An isolated fragment of the polypeptide of SEQ ID NO: 2 having α-L-arabinofuranosidase B activity wherein the fragment is at least 200 amino acids in length.

8. The isolated fragment of claim 7, wherein the fragment having the α-L-arabinofuranosidase B activity is at least 300 amino acids in length.

9. The isolated fragment of claim 7, wherein the fragment having the α-L-arabinofuranosidase B activity is at least 400 amino acids in length.

10. The isolated fragment of claim 7, wherein the fragment having the α-L-arabinofuranosidase B activity is at least 500 amino acids in length.

* * * * *

SEQUENCE LISTING

<160> NUMBER OF SEQ ID NOS: 4

<210> SEQ ID NO 1
<211> LENGTH: 3107
<212> TYPE: DNA
<213> ORGANISM: Penicillium funiculosum
<220> FEATURE:
<221> NAME/KEY: promoter
<222> LOCATION: (1)..(844)
<220> FEATURE:
<221> NAME/KEY: misc_feature
<222> LOCATION: (212)..(216)
<223> OTHER INFORMATION: Site creA
<220> FEATURE:
<221> NAME/KEY: misc_feature
<222> LOCATION: (403)..(408)
<223> OTHER INFORMATION: Site pacC
<220> FEATURE:
<221> NAME/KEY: misc_feature
<222> LOCATION: (559)..(564)
<223> OTHER INFORMATION: Site creA
<220> FEATURE:
<221> NAME/KEY: misc_feature
<222> LOCATION: (616)..(620)
<223> OTHER INFORMATION: Site AlcR
<220> FEATURE:
<221> NAME/KEY: TATA_signal
<222> LOCATION: (739)..(742)
<220> FEATURE:
<221> NAME/KEY: CDS
<222> LOCATION: (845)..(2368)
<220> FEATURE:
<221> NAME/KEY: terminator
<222> LOCATION: (2369)..(3107)
<220> FEATURE:
<221> NAME/KEY: polyA_signal
<222> LOCATION: (2460)..(2465)
<220> FEATURE:
<221> NAME/KEY: sig_peptide
<222> LOCATION: (845)..(926)

<400> SEQUENCE: 1

```
agtgattgat cattacagtc ggcaaaaacg gtccgtttat ccccggatga gcatgcgcga      60
agttgattag attgcaatcg gataaattgc attgcatgac tacgtgcctc ggcaaagatg     120
gacctcatcg agtgtatgag ctcggcattc aagtttaaag agtaatttaa ccttggggat     180
caaggacaag gcttttttaag cttatatgcg aggatccggg gccccagggt gccatgactc     240
ctcaacattc tgtttcaatt ggccaattgc ccctcctgag accctataac acgcggcgtt     300
ttcttctcct cttgggcaag cttagttgtg ctcaaatcgc tgtacctgaa ttaggcaggt     360
actcggcact cacacctatg atatcgtggc ctggtctaac ttgccaggaa atcggaattt     420
tcagactctt tttcttgccg atttgggatc aatcctaatt ttagttgcat caaggtaata     480
aacggaacac tttgttccac ctctgatgct cgtgagaaat agccttacac gcgtcacaag     540
gcttttgttt atgcaacgct ggagagggac agcatcgttt ttctccacgt tttttcaaat     600
tcttctgaat gcaccccgca taacggtaat tagcattagc attgtatgca tatcgagttt     660
gtaattattg gagggatttc atgccacctg agtaaaatga gccggtctga atctggttct     720
cggtagtttg aaaatgatta taaaagatag gtttcggctt gaaacgtgct ctgcttcagt     780
agtcgattaa gcctctcatc gatcatctta tagtcacagg cgtgctcgtc tagcaaaagt     840 catc atg ttt cca aga ata aaa cca gaa cgc acc agc ctg ttc gcc ctt     889
     Met Phe Pro Arg Ile Lys Pro Glu Arg Thr Ser Leu Phe Ala Leu
       1               5                  10                  15 ggc ctt ctt gcc tcg agc tcc ctt gtc acc gca act ggg cct tgc gat     937
Gly Leu Leu Ala Ser Ser Ser Leu Val Thr Ala Thr Gly Pro Cys Asp
```

|  |  |  |  |  |  |  |  |  |  |  |  |  |  |  |  |
|---|---|---|---|---|---|---|---|---|---|---|---|---|---|---|---|
|  |  |  | 20 |  |  |  |  | 25 |  |  |  |  | 30 |  |  |

```
atc tac tcc tcc ggc ggt acg cct tgc gtt gcc gcg cac agc acc acc    985
Ile Tyr Ser Ser Gly Gly Thr Pro Cys Val Ala Ala His Ser Thr Thr
             35                  40                  45 cgt gcc ctt tat gcc tct tac agc ggc gca ctc tac cag gtc aag cgg   1033
Arg Ala Leu Tyr Ala Ser Tyr Ser Gly Ala Leu Tyr Gln Val Lys Arg
         50                  55                  60 ggc tcc gac ggt gct aca acc acc atc tcg ccg ctt tcc gca ggt ggt   1081
Gly Ser Asp Gly Ala Thr Thr Thr Ile Ser Pro Leu Ser Ala Gly Gly
     65                  70                  75 gtc gcc aac gct gcc gcc caa gat acc ttc tgt gcc aac acg acc tgc   1129
Val Ala Asn Ala Ala Ala Gln Asp Thr Phe Cys Ala Asn Thr Thr Cys
 80                  85                  90                  95 ctc atc acg atc atc tac gac caa tcc ggc cgc ggt aac cat ctc acc   1177
Leu Ile Thr Ile Ile Tyr Asp Gln Ser Gly Arg Gly Asn His Leu Thr
                100                 105                 110 cag gct ccc ccc ggt ggc ttc gat ggc cct gac gtc aat ggc tat gat   1225
Gln Ala Pro Pro Gly Gly Phe Asp Gly Pro Asp Val Asn Gly Tyr Asp
            115                 120                 125 aac ttg gct ggc gcg att ggc gca ccc gtc act ctg aac ggt cag aag   1273
Asn Leu Ala Gly Ala Ile Gly Ala Pro Val Thr Leu Asn Gly Gln Lys
        130                 135                 140 gcg tac ggt gtc ttc atc tca cct ggt acc ggc tac cgt aac aac gct   1321
Ala Tyr Gly Val Phe Ile Ser Pro Gly Thr Gly Tyr Arg Asn Asn Ala
    145                 150                 155 gcc agc ggc aca gct acc ggt gac gca gcg gag ggc atg tat gca gtg   1369
Ala Ser Gly Thr Ala Thr Gly Asp Ala Ala Glu Gly Met Tyr Ala Val
160                 165                 170                 175 ctc gac gga act cac tac aac ggc gcg tgc tgc ttc gat tat ggc aat   1417
Leu Asp Gly Thr His Tyr Asn Gly Ala Cys Cys Phe Asp Tyr Gly Asn
                180                 185                 190 gcc gag acc agc agc act gat act ggc aat ggc cac atg gag gct atc   1465
Ala Glu Thr Ser Ser Thr Asp Thr Gly Asn Gly His Met Glu Ala Ile
            195                 200                 205 tac tat ggt gac gcc acc tac tgg gga agt ggc tcc ggc agc ggg cca   1513
Tyr Tyr Gly Asp Ala Thr Tyr Trp Gly Ser Gly Ser Gly Ser Gly Pro
        210                 215                 220 tgg gtc atg gct gat ctt gag aac ggt ctg ttc tct ggt gag agc act   1561
Trp Val Met Ala Asp Leu Glu Asn Gly Leu Phe Ser Gly Glu Ser Thr
    225                 230                 235 ggc gtg aac tct gcc gac ccg tct ctc tct tac cgc ttc gtc act gcg   1609
Gly Val Asn Ser Ala Asp Pro Ser Leu Ser Tyr Arg Phe Val Thr Ala
240                 245                 250                 255 gtc gtc aag ggt gag cca aat ttc tgg gct att cgc ggt ggt aac gct   1657
Val Val Lys Gly Glu Pro Asn Phe Trp Ala Ile Arg Gly Gly Asn Ala
                260                 265                 270 gca tcc ggt tct ttg tcc acg tac tac agt ggg gtg cgc cca caa gta   1705
Ala Ser Gly Ser Leu Ser Thr Tyr Tyr Ser Gly Val Arg Pro Gln Val
            275                 280                 285 tct ggc tat tac ccc atg cac aaa gaa ggt gcc atc att ctc ggc att   1753
Ser Gly Tyr Tyr Pro Met His Lys Glu Gly Ala Ile Ile Leu Gly Ile
        290                 295                 300 ggt ggt gat aac agc aac ggc gcc cag ggc acg ttc tac gaa ggt gtc   1801
Gly Gly Asp Asn Ser Asn Gly Ala Gln Gly Thr Phe Tyr Glu Gly Val
    305                 310                 315 atg acc tcc gga tat cca aca gac gcc acc gag aac tca gtg cag gct   1849
Met Thr Ser Gly Tyr Pro Thr Asp Ala Thr Glu Asn Ser Val Gln Ala
320                 325                 330                 335 aac atc gta gct gcc aaa tac gct acc acg tcg ttg acc agt ggt ccg   1897
Asn Ile Val Ala Ala Lys Tyr Ala Thr Thr Ser Leu Thr Ser Gly Pro
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 340 |     |     |     |     | 345 |     |     |     |     | 350 |     |      |
| gca | ctc | aca | gtc | ggc | tcc | gct | att | tcg | ttg | cat | gtc | acc | act | gcc | gga | 1945 |
| Ala | Leu | Thr | Val | Gly | Ser | Ala | Ile | Ser | Leu | His | Val | Thr | Thr | Ala | Gly |      |
|     |     |     | 355 |     |     |     |     | 360 |     |     |     |     | 365 |     |     |      |
| tac | acg | aca | cgc | tat | atc | gca | cac | aac | gac | acc | acc | gtc | aac | acc | cag | 1993 |
| Tyr | Thr | Thr | Arg | Tyr | Ile | Ala | His | Asn | Asp | Thr | Thr | Val | Asn | Thr | Gln |      |
|     |     | 370 |     |     |     |     | 375 |     |     |     |     | 380 |     |     |     |      |
| gtc | gtc | tca | tcg | tcc | agc | tct | acc | act | ctc | aaa | gag | caa | gct | agc | tgg | 2041 |
| Val | Val | Ser | Ser | Ser | Ser | Ser | Thr | Thr | Leu | Lys | Glu | Gln | Ala | Ser | Trp |      |
|     | 385 |     |     |     |     | 390 |     |     |     |     | 395 |     |     |     |     |      |
| acg | gtt | cgc | acc | ggt | ctt | ggc | aac | agc | gcc | tgt | ttc | tcg | ttt | gag | tcc | 2089 |
| Thr | Val | Arg | Thr | Gly | Leu | Gly | Asn | Ser | Ala | Cys | Phe | Ser | Phe | Glu | Ser |      |
| 400 |     |     |     | 405 |     |     |     |     | 410 |     |     |     |     | 415 |     |      |
| gtt | gac | acc | ccc | ggc | agc | tac | att | cgt | cac | tac | aac | ttc | gag | ctc | ctg | 2137 |
| Val | Asp | Thr | Pro | Gly | Ser | Tyr | Ile | Arg | His | Tyr | Asn | Phe | Glu | Leu | Leu |      |
|     |     |     | 420 |     |     |     |     | 425 |     |     |     |     | 430 |     |     |      |
| ctc | aat | gct | aat | gat | ggc | acc | aag | cag | ttc | cat | gaa | gat | gcc | aca | ttc | 2185 |
| Leu | Asn | Ala | Asn | Asp | Gly | Thr | Lys | Gln | Phe | His | Glu | Asp | Ala | Thr | Phe |      |
|     |     | 435 |     |     |     |     | 440 |     |     |     |     | 445 |     |     |     |      |
| tgc | ccg | cag | tct | ggc | ctt | agc | ggc | acg | ggt | acc | tcg | ctt | cga | agc | tgg | 2233 |
| Cys | Pro | Gln | Ser | Gly | Leu | Ser | Gly | Thr | Gly | Thr | Ser | Leu | Arg | Ser | Trp |      |
|     | 450 |     |     |     |     | 455 |     |     |     |     | 460 |     |     |     |     |      |
| agc | tat | ccc | acc | cgc | tat | ttc | cga | cac | tat | aat | aac | gta | ttg | tat | gct | 2281 |
| Ser | Tyr | Pro | Thr | Arg | Tyr | Phe | Arg | His | Tyr | Asn | Asn | Val | Leu | Tyr | Ala |      |
| 465 |     |     |     | 470 |     |     |     |     | 475 |     |     |     |     |     |     |      |
| gcc | agc | aac | ggc | ggc | gtg | caa | acg | ttt | gat | gcc | acc | gct | tcc | ttc | aac | 2329 |
| Ala | Ser | Asn | Gly | Gly | Val | Gln | Thr | Phe | Asp | Ala | Thr | Ala | Ser | Phe | Asn |      |
| 480 |     |     |     | 485 |     |     |     |     | 490 |     |     |     |     | 495 |     |      |
| gcc | gat | gtg | acc | ttc | ttg | gtc | gag | act | gcc | ttt | gca | tga | ttcttgacct |  |  | 2378 |
| Ala | Asp | Val | Thr | Phe | Leu | Val | Glu | Thr | Ala | Phe | Ala |     |     |     |     |      |
|     |     |     | 500 |     |     |     |     | 505 |     |     |     |     |     |     |     |      |

```
agcctcgtga aggtctaggt gtatggtaga accttgttag tgtatccttg gcacgattcg   2438
ttttaaatat aggcagattt aaataaactg atgattacaa agaagacttg gcttacctgt   2498
tagtaactat ctcaaagatg aagttgctgt ttgttgtagg aagatgccct gcatgcaaac   2558
aaaacaaact tcttgggcga tgaaggtcac gtgactcgta gccggtattg attacctgtt   2618
tgggaaacat tcacgccaac aactccgagg caatagtcag gcttgcaacg ataccaaaga   2678
gaaagagaaa cggaggtttg tataagagaaa atattgtcta gcaaactgac agtgactcat   2738
tccaccaaaa tgtatgtatg agttggccat gctctaagag ttcctgtagg gcaaccactg   2798
gctctaattg gctgccgggc ggcttcctcc cacggacccg ccctccagat gatcgtagca   2858
agttgccgcc gattaatttg ccagccacct tccctctttc tctcagggtc tgtctgtctg   2918
tgttcgctgt tgttcctcct gccattcccc tctgctccca ttcggtctgt catcttttga   2978
atacccttttg aatattcttc gcgcacactg agtgcgccca ttattgtatt attatcgact   3038
ttgtcgtctc ttctcagact tttcgtgtgt ttttttgggt cttcgttatg ggtattccgt   3098
aagttgatc                                                          3107
```

<210> SEQ ID NO 2
<211> LENGTH: 507
<212> TYPE: PRT
<213> ORGANISM: Penicillium funiculosum

<400> SEQUENCE: 2

Met Phe Pro Arg Ile Lys Pro Glu Arg Thr Ser Leu Phe Ala Leu Gly
 1               5                  10                  15

Leu Leu Ala Ser Ser Ser Leu Val Thr Ala Thr Gly Pro Cys Asp Ile

-continued

```
                20                  25                  30
Tyr Ser Ser Gly Gly Thr Pro Cys Val Ala Ala His Ser Thr Thr Arg
                    35                  40                  45
Ala Leu Tyr Ala Ser Tyr Ser Gly Ala Leu Tyr Gln Val Lys Arg Gly
 50                  55                  60
Ser Asp Gly Ala Thr Thr Thr Ile Ser Pro Leu Ser Ala Gly Gly Val
 65                  70                  75                  80
Ala Asn Ala Ala Ala Gln Asp Thr Phe Cys Ala Asn Thr Thr Cys Leu
                    85                  90                  95
Ile Thr Ile Ile Tyr Asp Gln Ser Gly Arg Gly Asn His Leu Thr Gln
                    100                 105                 110
Ala Pro Pro Gly Gly Phe Asp Gly Pro Asp Val Asn Gly Tyr Asp Asn
                    115                 120                 125
Leu Ala Gly Ala Ile Gly Ala Pro Val Thr Leu Asn Gly Gln Lys Ala
                    130                 135                 140
Tyr Gly Val Phe Ile Ser Pro Gly Thr Gly Tyr Arg Asn Asn Ala Ala
145                 150                 155                 160
Ser Gly Thr Ala Thr Gly Asp Ala Ala Glu Gly Met Tyr Ala Val Leu
                    165                 170                 175
Asp Gly Thr His Tyr Asn Gly Ala Cys Cys Phe Asp Tyr Gly Asn Ala
                    180                 185                 190
Glu Thr Ser Ser Thr Asp Thr Gly Asn Gly His Met Glu Ala Ile Tyr
                    195                 200                 205
Tyr Gly Asp Ala Thr Tyr Trp Gly Ser Gly Ser Gly Ser Gly Pro Trp
                    210                 215                 220
Val Met Ala Asp Leu Glu Asn Gly Leu Phe Ser Gly Glu Ser Thr Gly
225                 230                 235                 240
Val Asn Ser Ala Asp Pro Ser Leu Ser Tyr Arg Phe Val Thr Ala Val
                    245                 250                 255
Val Lys Gly Glu Pro Asn Phe Trp Ala Ile Arg Gly Gly Asn Ala Ala
                    260                 265                 270
Ser Gly Ser Leu Ser Thr Tyr Tyr Ser Gly Val Arg Pro Gln Val Ser
                    275                 280                 285
Gly Tyr Tyr Pro Met His Lys Glu Gly Ala Ile Ile Leu Gly Ile Gly
                    290                 295                 300
Gly Asp Asn Ser Asn Gly Ala Gln Gly Thr Phe Tyr Glu Gly Val Met
305                 310                 315                 320
Thr Ser Gly Tyr Pro Thr Asp Ala Thr Glu Asn Ser Val Gln Ala Asn
                    325                 330                 335
Ile Val Ala Ala Lys Tyr Ala Thr Thr Ser Leu Thr Ser Gly Pro Ala
                    340                 345                 350
Leu Thr Val Gly Ser Ala Ile Ser Leu His Val Thr Thr Ala Gly Tyr
                    355                 360                 365
Thr Thr Arg Tyr Ile Ala His Asn Asp Thr Thr Val Asn Thr Gln Val
                    370                 375                 380
Val Ser Ser Ser Ser Thr Thr Leu Lys Glu Gln Ala Ser Trp Thr
385                 390                 395                 400
Val Arg Thr Gly Leu Gly Asn Ser Ala Cys Phe Ser Phe Glu Ser Val
                    405                 410                 415
Asp Thr Pro Gly Ser Tyr Ile Arg His Tyr Asn Phe Glu Leu Leu Leu
                    420                 425                 430
Asn Ala Asn Asp Gly Thr Lys Gln Phe His Glu Asp Ala Thr Phe Cys
                    435                 440                 445
```

-continued

```
Pro Gln Ser Gly Leu Ser Gly Thr Gly Thr Ser Leu Arg Ser Trp Ser
    450                 455                 460

Tyr Pro Thr Arg Tyr Phe Arg His Tyr Asn Asn Val Leu Tyr Ala Ala
465                 470                 475                 480

Ser Asn Gly Gly Val Gln Thr Phe Asp Ala Thr Ala Ser Phe Asn Ala
                485                 490                 495

Asp Val Thr Phe Leu Val Glu Thr Ala Phe Ala
            500                 505

<210> SEQ ID NO 3
<211> LENGTH: 28
<212> TYPE: DNA
<213> ORGANISM: Artificial Sequence
<220> FEATURE:
<223> OTHER INFORMATION: Description of the Artificial Sequence: Primer
      XbaI-abfB

<400> SEQUENCE: 3
tctagaatgt ttccaagaat aaaaccag                                    28

<210> SEQ ID NO 4
<211> LENGTH: 23
<212> TYPE: DNA
<213> ORGANISM: Artificial Sequence
<220> FEATURE:
<223> OTHER INFORMATION: Description of the Artificial Sequence: Primer
      HindIII-abfB

<400> SEQUENCE: 4
aagctttcat gcaaaggcag tct                                         23
```